United States Patent [19]
Toyoda et al.

[11] Patent Number: 5,188,626
[45] Date of Patent: Feb. 23, 1993

[54] DISPOSABLE DIAPERS

[75] Inventors: Harumitsu Toyoda, Utsunomiya; Masamichi Senoo, Ichikai; Keiji Abe, Mouka, all of Japan

[73] Assignee: Kao Corporation, Tokyo, Japan

[21] Appl. No.: 575,619

[22] Filed: Aug. 31, 1990

[30] Foreign Application Priority Data

Dec. 26, 1989 [JP] Japan .................................. 1-337066
Mar. 20, 1990 [JP] Japan .................................. 2-70360

[51] Int. Cl.$^5$ ............................................ A61F 13/15
[52] U.S. Cl. .................................. 604/385.1; 604/358
[58] Field of Search ...................... 604/385.1, 378, 381, 604/385.2

[56] References Cited

U.S. PATENT DOCUMENTS

| | | | |
|---|---|---|---|
| 4,352,356 | 10/1982 | Tong | 604/402 |
| 4,681,580 | 7/1987 | Reising et al. | 604/385.1 |
| 4,861,652 | 8/1989 | Lippert et al. | 604/385.1 |
| 4,935,021 | 6/1990 | Huffman et al. | 604/385.1 |
| 4,946,454 | 8/1990 | Schmidt | 604/385.1 |

FOREIGN PATENT DOCUMENTS

| | | |
|---|---|---|
| 59-144601 | 8/1984 | Japan . |
| 60-17101 | 1/1985 | Japan . |
| 61-275402 | 12/1986 | Japan . |
| 62-223303 | 10/1987 | Japan . |

Primary Examiner—Randy C. Shay
Assistant Examiner—Gina M. Gualtieri
Attorney, Agent, or Firm—Birch, Stewart, Kolasch & Birch

[57] ABSTRACT

A disposable diaper having a liquid pervious top-sheet, a liquid impervious and vapor pervious backsheet and an absorbent core interposed between the topsheet and the backsheet comprising interposing liquid impervious and vapor pervious barrier sheets between the topsheet and the backsheet, said barrier sheets being extended from the front edge and the rear edge of the diaper to the inwards of the front edge and the rear edge of the absorbent core respectively, to thereby form waist barrier parts covering the front edge and the rear edge of the absorbent core, and the barrier sheets being so formed that the intensity in the lateral direction of the diaper is higher than the intensity in the longitudinal direction of the diaper.

5 Claims, 3 Drawing Sheets

DISPOSABLE DIAPERS

BACKGROUND OF THE INVENTION

1. Field of the Invention

This invention relates to disposable diapers, and more particularly to disposable diapers which are capable of arresting a leakage of urine and other fluids discharged from the body in the waist part and preventing diaper rash in the waist part, and which have improved strength and enhanced fit to the wearer in the waist portion.

2. Description of the Prior Art

It is well known that conventional paper diapers (disposable diapers) are generally superior to cloth diapers in adsorbability, in water retentivity and in a capacity of waste materials. Examples of known disposal diapers are disclosed in Japanese Laid-open Publications Nos. 58-54002, 59-144601, 60-17101, 62-223303 and 61-275402.

Japanese Laid-open Publication No. 58-54002 discloses a disposable diaper which has a liquid pervious topsheet, a liquid impervious backsheet and a water impermeable plastic sheet interposed between both sheets at the edge of the absorbent core in the waist part to thereby prevent urine and other fluids leaking from the edge of the absorbent core.

Japanese Laid-open Publication Nos. 59-144601 and 60-17101 disclose disposable diapers which have an elastically expansible member of heat contractibility around the waist part thereby improving the fit with the waist portion and protecting an undergarment from wetting with a leakage of urine and other fluids.

Japanese Laid-open Publication No. 62-223303 discloses a disposable diaper which has an elastically expansible member of polyurethane foam around the waist part to thereby enhance the fit. This disposable diaper intends to prevented waste materials from wetting the undergarment when tucking clothes, especially an undergarment, between the front waist flap part and the infant's body.

Japanese Laid-open Publication No. 61-275402 discloses a disposable diaper which adapts the advantages of the above-mentioned two disposable diapers. Between a liquid permeable topsheet and a liquid impermeable backsheet, at least one unitary waistshield and an elastically expansible waistband are interposed thereby preventing the fluids which migrate toward the perimeter of the diaper from wetting the wearer's undergarment.

However, the disposable diaper disclosed in Japanese Laid-open Publication No. 58-54002 has such a problem that a space occurs around the waist portion depending on the wearing condition of an infant, and if the waist portion is so fastened as not to provide a space, the infant receives pressure. Further, even if there is no space, the infant may move so hard that the figure of the infant changes according to the physical activity or movements, and a diaper will become out of shape and slip out of place. Thus a space occurs around the waist portion, and urine and other fluids are liable to leak due to the lack of the fit to the waist portion of the infant.

Recently, as a backsheet, a vapor pervious film tends to be used for preventing stuffiness; the vapor pervious film being obtained by stretching polyolephin resin to which an inorganic filler is added. However, the strength in the lateral direction of disposable diapers is low, and the strength in the lateral direction of nonwoven fabric generally used as a topsheet is low, too. Therefore, a problem occurs when the adhesive tape of the diaper is tightly stretched or the waist size expands according to the activity, a tension works on both of the back and top-sheets to tear the sheets longitudinally. In this case, even if a vapor pervious barrier sheet comprising the same material as a backsheet is placed to attempt to enhance the strength, the tension works on the non-connected portion of the topsheet, the barrier sheet and the backsheet, and the barrier sheet intermediate resists the tension. Therefore, it is a problem that when the lateral strength of the barrier sheet is low, even the barrier sheet tears and a leakage occurs.

In each of the disposable diapers disclosed in Japanese Laid-open Publications Nos. 59-144601 and 60-17101, an elastically expansible member is so interposed in the lateral direction between the topsheet and the backsheet as to ventilate and prevent stuffiness. However, it is a problem that urine and other fluids are likely to leak from the ventilation part and a leakage out of the waist portion cannot be prevented.

The disposable diaper disclosed in Japanese Laid-open Publication No. 62-223303 can prevent an undergarment from wetting when the undergarment is tucked into the space between the diaper and the body. However, it is a problem that urine and other fluids cannot be efficiently prevented from leaking out of the edge of the absorbent core.

It is a problem of the disposable diaper disclosed in Japanese Laid-open Publication No. 61-275402 that the waist gather in the waistband part does not fit so closely to the waist portion as to prevent urine and other fluids from leaking out of the absorbent core. Therefore, urine and other fluids are liable to leak through the waist gather part, and the intended object cannot be completely achieved.

SUMMARY OF THE INVENTION

Accordingly, an object of the present invention is to provide a disposable diaper which is capable of arresting a leakage of waste materials from the waist portion through the front and rear edge parts of the absorbent core, preventing an undergarment wetting due to the tucking of the undergarment into a space of the waist portion and preventing the stuffiness and diaper rash in the waist portion, and which is so strong in the longitudinal direction as to make affixing means such as a tape fastener function sufficiently.

The above-mentioned object is achieved by providing a disposable diaper having a liquid pervious topsheet, a liquid impervious and vapor pervious backsheet and an absorbent core interposed between the topsheet and the backsheet, said disposable diaper comprising liquid impervious and vapor pervious barrier sheets interposed between the topsheet and the backsheet, said barrier sheets being extended from the front edge and the rear edge of the diaper inwards to the front edge and the rear edge of the absorbent core respectively, to thereby form waist barrier parts covering the front edge and the rear edge of the absorbent core, and said barrier sheets being so formed that the strength in the lateral direction of the diaper is higher than the strength in the longitudinal direction of the diaper.

According to the disposable diaper of the present invention, a waist barrier sheet can reliably resist tension in the lateral direction acting to the backsheet side or the topsheet side of the waist part to thereby prevent

DETAILED DESCRIPTION OF THE EMBODIMENT

The present invention will be described hereunder according to FIG. 1 through FIG. 9.

Figure 1:
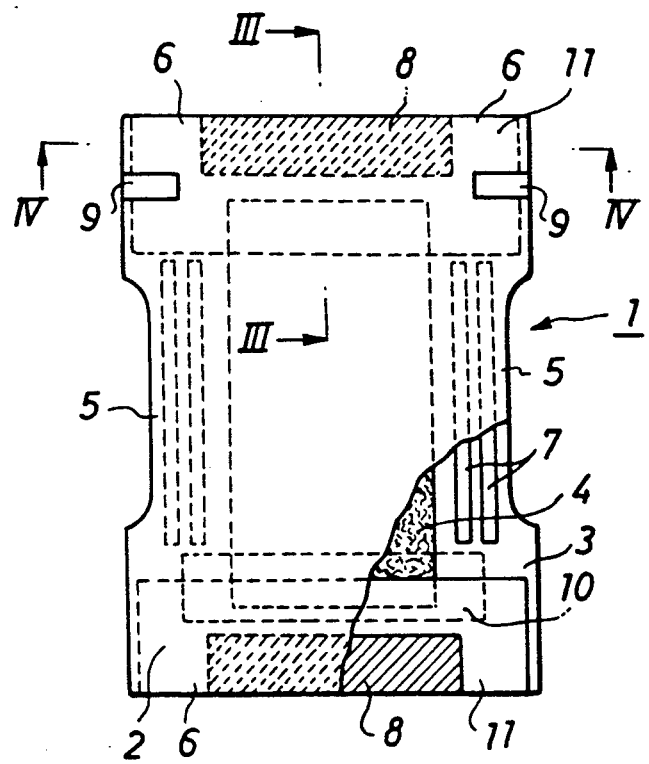
FIG. 1 is a partially cut-away plan view showing the development surface of one embodiment of the disposal diaper of the present invention.
Figure 2:
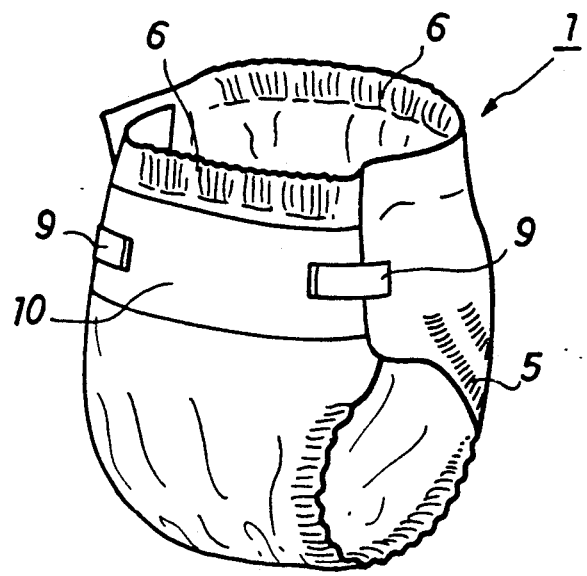
FIG. 2 is a perspective view of the disposable diaper in FIG. 1 when it is assembled on a wearer, not shown, in the standing position.

The disposable diaper 1 of the embodiment of the present invention, as shown in FIG. 1 and FIG. 2, comprises a liquid pervious topsheet 2, a liquid impervious and vapor pervious backsheet 3, and an absorbent core 4 interposed between the topsheet 2 and the backsheet 3. The topsheet 2 and backsheet 3 extend outwardly from the surroundings of the absorbent core 4 to form side flap parts 5, 5 in the extended parts of both longitudinal sides of the absorbent core 4 and waist flap parts 6, 6 in the extended parts from both the front and rear edges of the absorbent core 4. In the side flap parts 5, 5 between the topsheet 2 and backsheet 3, elastically expansible members 7, 7 are disposed, and in the waist flap parts 6, 6 between the topsheet 2 and backsheet 3, elastically expansible members 8, 8 are disposed. In FIG. 1 the elastically expansible members 7, 7 and 8, 8 are adhered with adhesive in the stretched state. Therefore, when the disposable diaper 1 of the present invention is used, as shown in FIG. 2, the elastically expansible members 7 and 8 shrink to thereby form gathers in the side flap parts 5, 5 and in the waist flap parts 6, 6. In both of the lateral sides of the waist flap part 6 on the rear side (back side), attaching members 9, 9 comprising a tape fastener, e.g. an adhesive tape or the like, are disposed in a manner as described below. In the backsheet 3 of the waist flap part 6 on the front side (stomach side), a target sheet 10, to which the attaching members 9, 9 affix, comprising a tape the surface of which is smooth, e.g. a landing tape or the like is disposed along with the elastically expansible member 8. The target sheet 10 is located nearer to the absorbent core than to the elastically expansible member 8. The attaching members 9, 9 and the target sheet 10 are affixed in the waist part when the disposable diaper 1 is worn (see FIG. 2).

Figure 3:
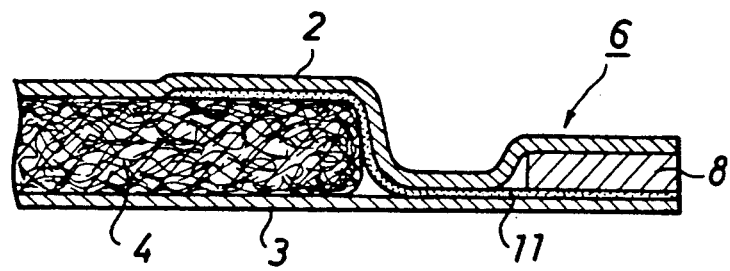
FIG. 3 is a sectional view on the line III—III in FIG. 1.
Figure 4:
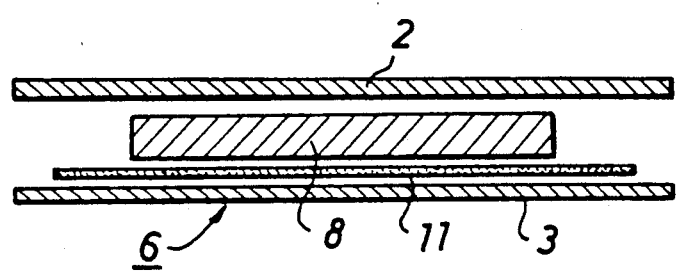
FIG. 4 is a sectional view on the line IV—IV in FIG. 1.

Accordingly, in the disposable diaper 1 of the present invention, a liquid impervious and vapor pervious barrier sheet 11 interposed between the topsheet 2 and backsheet 3 is stretched from each of the front and rear edge parts of the waist flap parts 6, 6 through each of the insides of the front and rear edge parts of the absorbent core 4 and covers each of the front and rear edge parts of the absorbent core 4 as shown in FIG. 3, so that the waist barrier part which prevents waste materials such as urine absorbed in the absorbent core 4 from leaking out of the front and rear fringe of the absorbent core 4 to the waist flap parts is formed.

The barrier sheet 11 is formed to be a rectangular sheet. The longitudinal length of the sheet has the length from waist flap part 6 through the inside of the rear edge part of the absorbent core 4 as mentioned above, and the lateral length of the sheet is generally equal to the width of the waist flap part 6 (see FIG. 1 to FIG. 4). The barrier sheet 11 is so disposed as to overlap with the absorbent body 4 in the surface side thereof as well as with the backsheet 3 of the waist flap part 6. Further, in the waist flap part 6 of the barrier sheet 11 the elastically expansible member 8 is placed apart from the rear edge part of the absorbent core to thereby form a space between the absorbent core 4 and the flexible elastic material 8. The width of the space is preferably at least 5 mm or more, so as to make a waist gather, more preferably 10 to 20 mm. If the width is less than 5 mm, it is not preferable because the wrinkle of the waist gather formed by the elastically expansible member 8 reaches the affixed portion of the attaching members 9, 9.

Further, the attaching members 9, 9 are located in the both ends of the space, and the target sheet 10 is located apart from the waist gather part. The attaching members 9, 9 and the target sheet 10 are so independent from the waist gather part that the wrinkle does not reach thereto and the attaching members 9, 9 are capable of affixing to the target sheet 10, the surface of which is smooth. In addition, the attaching members 9, 9 can reliably fasten the wearer's waist in the waist gather part (see FIG. 2).

Accordingly, the barrier sheet 11 used in the disposable diaper 1 of the embodiment of the present invention, as mentioned above, comprises a liquid impervious and vapor pervious sheet, so that the sheet can prevent liquid leaking, as well as stuffiness and diaper rash, because vapor is pervious. Conventional sheets can be used as the above-mentioned sheet. An example includes a moisture permeable film obtained by stretching polyolephine resin to which inorganic filler is added. Although the moisture permeable film is used as a backsheet of the disposable diaper 1, the strength in the stretched direction is high, whereas the lateral strength is low, so that the film is easy to tear. Therefore, the object of the present invention cannot be achieved by using such a film as a barrier sheet. However, in this case, by using the laterally stretched sheet, that is, turning laterally stretched sheet by an angle of 90 degrees in the producing process of diapers and inserting the re-oriented and laterally stretched sheet into the diaper, the resulting lateral strength of the diapers can be improved. Further, vapor pervious film produced by an alternative method such as a biaxial stretching method can be used, too. According to this method, without introducing the above-mentioned special process of re-orienting a laterally stretched sheet by 90 degrees for producing diapers, the barrier sheet with high lateral strength can also be obtained.

Further, no limitation to the elastically expansible members 7 and 8 is applied if materials are elastic members having expansibility and contractibility. Examples include a thready elastic body comprising polyurethane elastic fiber and natural rubber, a filmy elastic body or polyurethane film. It is preferable to use the filmy elastic body or the thready elastic body as the elastically expansible member 7. It is preferable to dispose single or plural filmy elastic bodies having a width of 5 to 20 mm, or plural thready elastic bodies having a width of 5 to 25 mm.

It is preferable to use polyurethane foam as the elastically expansible member 8. It is preferably 1 to 3 mm in thickness and at least 5 mm in width, more preferably 10 to 20 mm in width. When polyurethane foam is used, it is preferable that the density of foam is so adjusted as to be 20 to 70 kg/m$^3$ and that the foam is preferably open cell.

Further, the conventional sheets can be used as the liquid pervious topsheet 2 and the liquid impervious and vapor pervious backsheet used in the disposable diaper 1 of the embodiment of the present invention.

The disposable diaper 1 of the present embodiment has the above-mentioned constitution, so that urine or other fluids in the waist flap parts 6, 6 can be prevented by the barrier sheets 11, 11, and stuffiness and diaper rash can be efficiently prevented. In addition, the fastening position of the attaching member 9, 9 and the waist gather part work independently, so that the waist gather parts 6, 6 fit the waist portion closely and do not twist, or a space into which an undergarment is tucked does not occur between the waist gather parts 6, 6 and the wearer's waist portion. Therefore, there is no fear of wetting the undergarment. The wrinkle of the waist gather part does not reach the target sheet 10 so that the attaching members 9, 9 always affix to the target sheet 10, without a fear of slipping out. Therefore, the disposable diaper 1 can be reliably adapted to an infant who is always in hard activity. Further, there is no fear of tearing the waist flap parts 6, 6, even if the high tension acts thereto in use.

Figure 5:
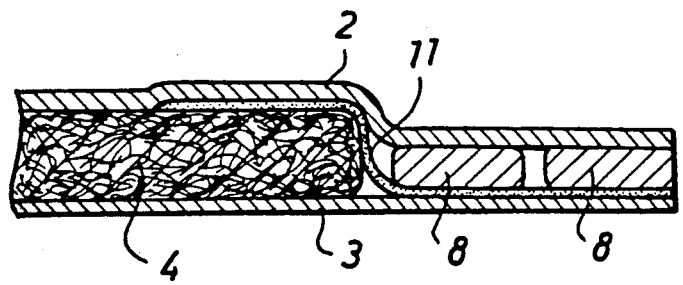
FIG. 5 is a view corresponding to FIG. 3, showing the other embodiment of the disposable diaper.

FIG. 5 shows another embodiment of the disposable diaper of the present invention. The disposable diaper of this embodiment has the same aforementioned constitution except that two pieces of elastically expansible member 8 are placed in each waist flap parts 6, 6, so that the same function and associated advantages and effects are to be expected.

Figure 6:
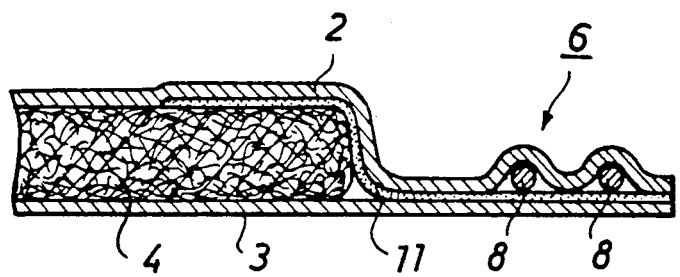
FIG. 6 and FIG. 7 are partial sectional views corresponding to FIG. 3, each showing the relevant part of the other embodiment.

Further, the disposable diaper of the embodiment shown in FIG. 6 has basically the same constitution as the disposable diaper of the aforementioned embodiment, except that the waist gather is made of two thready elastic bodies.

Figure 7:
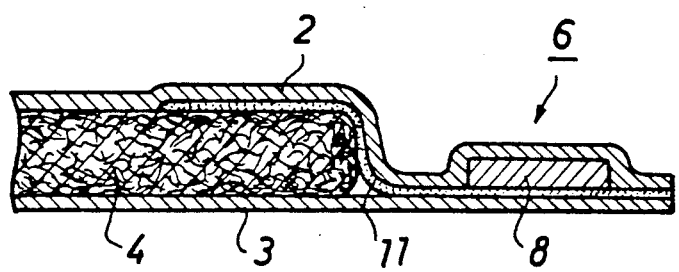

Furthermore, the disposable diaper of the embodiment shown in FIG. 7 has basically the same constitution as the disposable diaper of the aforementioned embodiment, except that the waist gather part 6 is made of a filmy elastic body.

The diapers of the embodiments shown in FIGS. 1 through 4, 6 and 7 can prevent the waist gather part from bending when packed up for shipping.

That is, it is a conventional packing manner that a diaper folds in thirds in the lateral direction and then folds in thirds in the longitudinal direction to make a rectangular shape for packing in each bag.

Figure 8:
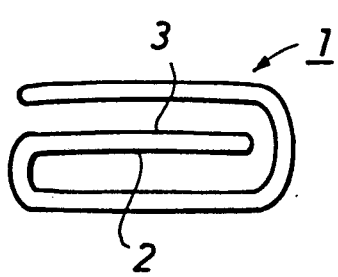
FIG. 8 and FIG. 9 are views each showing an outline of the folded disposable diaper.

The outline of the diaper folded in a rectangular shape is shown in FIG. 8, wherein the line shows the diaper folded in a narrow-width shape.

Figure 9:
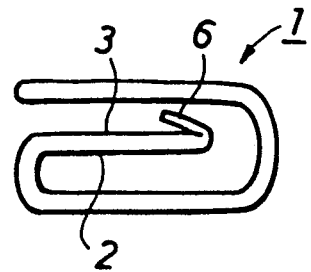

When the diaper is folded in the shape shown in FIG. 8, it is a conventional manner that the target sheet 10 side comes inside in order to keep the sheet from getting dirty. The problem of this case is that the waist flap part 6 folds outwardly and the folded line is fixed as shown in FIG. 9, so that the waist gather does not function efficiently.

However, in the disposable diaper 1, the waist gather part is separated from the absorbent core 4, so that it is freely folded in the region between both parts, and the waist gather itself does not bends or twist, even if the waist flap 6 bend outwardly. Therefore, in view of the above, and, in the disposable diaper 1, the waist gather closely fits the waist portion of the wearer.

No limitation to disposable diapers is intended and any disposable diaper within the scope of the present invention can be included in the present invention.

What is claimed is:

1. A disposable diaper having a liquid pervious topsheet, a liquid impervious and vapor pervious backsheet and an absorbent core interposed between the topsheet and the backsheet, with an inside surface of the core adjacent the topsheet and an outside surface of the core adjacent the backsheet, said disposable diaper comprising:

liquid impervious and vapor pervious barrier sheets interposed between the topsheet and the backsheet, one of said barrier sheets being extended from a front edge of the backsheet of the diaper and a second one of said barrier sheets being extended from a rear edge of the backsheet of the diaper to a front edge and rear edge of the inside surface of the absorbent core respectively, thereby forming waist barrier parts covering the front edge and the rear edge of the absorbent core, and said barrier sheets being prestretched in a lateral direction of the diaper; such that a strength in a lateral direction of the diaper is higher than a strength in a longitudinal direction of the diaper.

2. The disposable diaper according to claim 1, wherein the strength in a lateral direction of the barrier sheet of the diaper is higher than the strength in a lateral direction of the backsheet of the diaper.

3. The disposable diaper according to claim 1, wherein an elastically expansible member is interposed in a lateral direction between said barrier sheet and top-sheet to thereby form a waist part which is capable of expansion and contraction.

4. The disposable diaper according to claim 3, wherein said elastically expansible member is disposed apart from the inside front and rear edges of said absorbent core.

5. The disposable diaper according to claims 3 or 4, wherein said elastically expansible member is polyurethane foam.

* * * * *